United States Patent
Drzewiecki

(12) 
(10) Patent No.: US 6,286,360 B1
(45) Date of Patent: Sep. 11, 2001

(54) METHODS AND APPARATUS FOR REAL TIME FLUID ANALYSIS

(75) Inventor: Tadeusz M. Drzewiecki, Rockville, MD (US)

(73) Assignee: Metasensors, Inc., Rockville, MD (US)

( * ) Notice: Subject to any disclaimer, the term of this patent is extended or adjusted under 35 U.S.C. 154(b) by 0 days.

(21) Appl. No.: 09/513,315

(22) Filed: Feb. 25, 2000

Related U.S. Application Data

(60) Provisional application No. 60/121,370, filed on Feb. 25, 1999.

(51) Int. Cl.[7] .............................. G01N 29/02; G01N 31/00
(52) U.S. Cl. ....................... 73/24.01; 73/23.01; 73/24.01; 73/54.02; 73/24.06; 702/24
(58) Field of Search ................... 73/54.02, 23.2, 73/24.01, 24.06, 24.05, 30.03, 54.24, 61.45, 61.47, 61.73, 861.61; 702/22, 23, 24, 25

(56) References Cited

U.S. PATENT DOCUMENTS

| | | |
|---|---|---|
| 3,270,960 | 9/1966 | Phillips . |
| 3,698,238 | 10/1972 | Wall et al. . |
| 3,765,224 | 10/1973 | Ostdiek et al. . |
| 3,771,348 * | 11/1973 | Villarroel ............................ 73/31.04 |
| 3,791,200 | 2/1974 | Hayre . |
| 3,808,877 | 5/1974 | Blair . |
| 3,839,914 | 10/1974 | Modisette et al. . |
| 3,927,670 | 12/1975 | Turney et al. . |
| 4,150,561 * | 4/1979 | Zupanick ............................ 73/24.01 |
| 4,150,670 | 4/1979 | Jewett et al. . |
| 4,167,873 | 9/1979 | Bahrton . |
| 4,196,626 | 4/1980 | Manion et al. . |
| 4,379,402 * | 4/1983 | Harmon, III ......................... 73/23.2 |
| 4,463,598 | 8/1984 | Haney . |
| 4,558,220 | 12/1985 | Evans . |
| 4,570,675 | 2/1986 | Fenwick et al. . |
| 4,627,271 | 12/1986 | Abbott et al. . |
| 4,634,053 | 1/1987 | Herzfeld et al. . |
| 4,665,911 | 5/1987 | Williams et al. . |
| 4,670,405 * | 6/1987 | Stetter et al. ......................... 73/23.2 |
| 4,779,451 | 10/1988 | Ezawa et al. . |
| 4,838,091 | 6/1989 | Markland et al. . |
| 4,847,783 | 7/1989 | Grace et al. . |
| 4,890,482 | 1/1990 | Maini . |

(List continued on next page.)

OTHER PUBLICATIONS

Calkins et al. A Flueric Respiratory and Anesthetic Gas Analyzer; Annals of Biomedical Engineering, vol. 10, pp. 83–96, 1982.

Togawa et al. Biomedical Transducers and Instruments; CRC Press LLC, 1997.

Calkins et al. A Flueric Respiratory and Anesthetic Gas Analyzer; Annals of Biomedical Engineering, vol. 10, pp. 83–96, 1982.

Togawa et al. Biomedical Transducers and Instruments; CRC Press LLC, 1997.

*Primary Examiner*—Hezron Williams
*Assistant Examiner*—Michael Cygan

(57) ABSTRACT

A gas analyzer (10) integrated into the main passageway (11) of a breathing circuit includes pressure-drop flow element (12) that measures a pressure drop across an orifice, an acoustic flowmeter (14) measures the speed of sound in the gas mixture, and a SAW device (20) from which the viscosity of the gas mixture is determined. The dielectric constant of the gas mixture is determined from the capacitance of spaced-apart charged plates of a capacitor (22) through which the mixture passes. The gas mixture density is determined from the measured pressure drop and flow rate, while the gas mixture specific heat is determined from the density and speed of sound in accordance with known relationships. The individual concentrations of five constituents of a mixture of gasses can be determined by solving five equations relating the independently measured properties of the gas mixture to the individual constituent concentrations.

41 Claims, 6 Drawing Sheets

U.S. PATENT DOCUMENTS

| | | | | |
|---|---|---|---|---|
| 4,907,441 | * | 3/1990 | Shurmer | 73/23.2 |
| 4,909,078 | | 3/1990 | Sittler et al. . | |
| 4,930,357 | | 6/1990 | Thurston et al. . | |
| 5,003,810 | | 4/1991 | Jepson et al. | 73/861.19 |
| 5,025,653 | | 6/1991 | Schuldt . | |
| 5,076,094 | * | 12/1991 | Frye et al. | 73/19.03 |
| 5,105,847 | | 4/1992 | Wood . | |
| 5,107,920 | | 4/1992 | Scotti et al. . | |
| 5,108,466 | | 4/1992 | Klein et al. . | |
| 5,221,871 | | 6/1993 | Fuchs et al. | 73/24.04 |
| 5,238,056 | | 8/1993 | Scotti et al. . | |
| 5,272,907 | * | 12/1993 | Hakala | 73/23.2 |
| 5,279,155 | | 1/1994 | Johnson et al. | 73/202.5 |
| 5,306,644 | * | 4/1994 | Myerholtz et al. | 73/61.45 |
| 5,311,447 | | 5/1994 | Bonne . | |
| 5,325,704 | | 7/1994 | Mariani et al. | 73/24.06 |
| 5,335,553 | | 8/1994 | Ueki et al. | 73/861.19 |
| 5,461,562 | | 10/1995 | Tabanou et al. . | |
| 5,465,608 | * | 11/1995 | Lokshin et al. | 73/24.01 |
| 5,469,369 | * | 11/1995 | Rose-Pehrsson et al. | 73/23.2 |
| 5,495,744 | | 3/1996 | Veda . | |
| 5,567,868 | | 10/1996 | Craig et al. | 73/23.42 |
| 5,635,650 | | 6/1997 | Ito | 73/861.21 |
| 5,640,995 | | 6/1997 | Packard et al. . | |
| 5,654,497 | | 8/1997 | Hoffheins et al. | 73/31.05 |
| 5,767,387 | | 6/1998 | Wang . | |
| 5,821,405 | | 10/1998 | Dickey et al. | 73/53.01 |
| 5,827,976 | | 10/1998 | Stouffer et al. | 73/861.19 |
| 6,028,307 | | 2/2000 | Young et al. . | |
| 6,076,392 | | 6/2000 | Drzewiecki | 73/23.2 |
| 6,116,080 | * | 9/2000 | Logue et al. | 73/24.05 |

* cited by examiner

METHODS AND APPARATUS FOR REAL TIME FLUID ANALYSIS

CROSS REFERENCE TO RELATED APPLICATIONS

This application claims priority from U.S. Provisional Patent Application Serial No. 60/121,370 entitled "Methods and Apparatus for Real Time Fluid Analysis", filed Feb. 25, 1999. The disclosure of this provisional application is incorporated herein by reference in its entirety.

BACKGROUND OF THE INVENTION

1. Field of the Invention

The present invention relates to methods and apparatus for real time fluid analysis and, more particularly, to a gas analyzer capable of determining concentrations of constituent gasses of a mixture as well as providing a direct quantitative measure of uptake, consumption and production of various inspired and respired gasses in real time.

2. Description of the Related Art

The determination of the relative concentrations of gasses in a mixture has been the subject of numerous inventions and intensive research over the years. Particularly, when noxious, poisonous or otherwise hazardous gasses are present, knowledge of the amount of such gasses is important to alert personnel in the area of any potential danger. In medical and clinical settings, awareness of the concentrations of respired gasses is important in the determination of patient metabolic conditions, especially the relative and absolute amounts of oxygen and carbon dioxide which provide information on the metabolization of oxygen as well as respiratory functioning. Under operating room conditions, anesthesiologists must be careful in administering anesthesia gasses and do so as a function of metabolic rate, and also must be aware of the absolute amount of anesthetic being provided in order to prevent overdosing or underdosing which would cause a patient to be aware during an operation. Also, when several different potent anesthetics must be administered during a procedure, the net amounts of the anesthetics need to be monitored to prevent overdosing.

Multiple medical gas monitors (MMGMs) continuously sample and measure inspired and exhaled (including end-tidal) concentrations of respiratory gasses, including anesthetic gasses during and immediately following administration of anesthesia. These monitors are required since an overdose of anesthetic agent, and/or too little oxygen, can lead to brain damage and death, whereas too little agent results in insufficient anesthesia and subsequent awareness. The current development of these monitoring devices is described in the extensive anesthesia and biomedical engineering literature. Complete and specific information about the principles and applications of these devices is well reviewed in several texts (see, e.g., Lake, *Clinical Monitoring*, WB Saunders Co., pp. 479–498 (ch. 8), 1990, incorporated herein by reference in its entirety), manufacturer's and trade publications (see, e.g., ECRI, "Multiple Medical Gas Monitors, Respired/Anesthetic", August 1983, incorporated herein by reference in its entirety), and in extensive anesthesia literature describing this equipment and its principles, methods and techniques of operation.

Medical gas monitoring provides the clinician with information about the patient's physiologic status, verifies that the appropriate concentrations of delivered gases are administered, and warns of equipment failure or abnormalities in the gas delivery system. These monitors display inspired and exhaled gas concentrations and may sound alarms to alert clinical personnel when the concentration of oxygen ($O_2$), carbon dioxide ($CO_2$), nitrous oxide ($N_2O$), or anesthetic agent falls outside the desired set limits.

Most MMGMs utilize side-stream monitoring wherein gas samples are aspirated from the breathing circuit through long, narrow-diameter tubing lines. it water trap, desiccant and/or filter may be used to remove water vapor and condensation from the sample before the gas sample reaches the analysis chamber. Gas samples are aspirated into the monitor at either an adjustable or a fixed flow rate, typically from 50 to 250 ml/min. Lower rates minimize the amount of gas removed from the breathing circuit and, therefore, from the patient's tidal volume; however, lower sampling flow rates increase the response time and typically reduce the accuracy of conventional measurements. These gas monitors eliminate the exhaust gas through a scavenging system or return certain gas constituents to the patient's breathing circuit.

Currently used anesthetic gas monitors employ one or a combination of methods and techniques to determine concentrations of respiratory gasses, including: mass spectroscopy, Raman spectroscopy, infrared light spectroscopy, photoacoustic spectroscopy, piezoelectric resonance, polarography, electrochemical fuel cells, paramagnetic analysis, and magnetoacoustics. Each of these techniques suffers from one or more limitations, including: the high cost and complexity of the equipment, the inability to provide real time measurements, the ability to measure concentration of only certain types of gasses or a limited number of gasses, inaccurate measurements, and the need for frequent equipment calibration. Another major disadvantage of most conventional gas monitors is that they do not measure nitrogen ($N_2$). Safety considerations require that the presence of nitrogen be detected, since nitrogen detection provides warning of air embolisms, as well as alerting to possible loss of integrity of the breathing circuit, as air (with $N_2$) is introduced. These conventional techniques and their drawbacks are described in U.S. patent application Ser. No. 09/104,997 to Drzewiecki (the present inventor), filed Jun. 26, 1998, entitled "Method and Apparatus for Real Time Gas Analysis, incorporated herein by reference in its entirety.

The Drzewiecki patent application relates to a universal method and apparatus for determining, in real time, the individual concentrations of fluid constituents of any mixture of a predetermined number of fluids (e.g., gasses or liquids) using, in the preferred embodiment, fluidic sensors. More specifically, the fluid (e.g., gas) analyzer disclosed therein comprises a side-stream sampling system, wherein a sample of the gas to be analyzed is drawn off (e.g., using a vacuum pump) and passed through fluidic oscillators, capillaries and an orifice which provide pressure drops and frequencies from which the properties (density, viscosity and specific heat) of the gas mixture can be determined in accordance with well-known relationships. The concentrations of the constituents are then derived from the measured mixture properties.

In particular, N equations, which from first principles, relate the individual fluid concentrations to measured properties of the mixture, are solved for the N unknown individual concentrations of the fluids in the mixture. N−1 properties of the mixture are measured by N−1 sensors, which from cost considerations are preferably fluidic sensors, but may be any other technology devices, and N−1 of the N equations are formed from the determined properties. The Nth equation is the constitutive equation, which requires that the sum of the unknown concentrations of the N known constituents be equal to unity.

While the fluid analysis techniques disclosed in the Drzewiecki patent application overcome virtually all of the limitations of the aforementioned conventional techniques, in certain cases, it is advantageous not to withdraw and analyze a side-stream sample in the manner described therein. Such situations include the monitoring of neonates whose tidal volume flow is so small that it approaches the required minimum side-stream sample flow, and cases where it is desirous to not operate a vacuum pump (because of noise or power considerations).

Moreover, in certain implementations, it may be advantageous to avoid side-stream sampling in order to integrate the gas analyzer into a monitoring system in a low cost manner with a minimum of sensors and complexity. For example, a gas analyzer employing the principles disclosed in the Drzewiecki patent application would be useful in a system for non-invasively monitoring metabolic rates, cardiac output and/or pulmonary function, such as that described in U.S. patent application Ser. No. 09/488,763 by Calkins et al., entitled "Non-Invasive Cardiac Output and Pulmonary Function Monitoring Using Respired Gas Analysis Techniques And Physiological Modeling", filed Jan. 21, 2000, incorporated herein by reference in its entirety. In this context, it would be desirable to integrate in a cost effective manner the sensors and elements required to determine gas concentrations with those capable of measuring end-tidal flow rates and volume in order to provide a direct quantitative measure of uptake, consumption and production of various inspired and respired gasses on a real time basis to support breath-by-breath determination of cardiac output and pulmonary function.

Further, the sensors used to measure the properties of fluid mixtures in the preferred embodiments described in the Drzewiecki patent application rely primarily upon fluidic elements. While these fluidic elements provide numerous benefits, in general, the sensors used to measure the properties of a gas mixture are not required to include fluidic elements. Indeed, in certain implementations, other type of elements may yield an overall simpler or lower cost design. Additionally, as alluded to the Drzewiecki patent application, properties other than those described in detail therein may be used to assay a gas mixture and to extend the fluid analysis principles disclosed therein to mixtures of a greater number of gasses.

SUMMARY OF THE INVENTION

Therefore, in light of the above, and for other reasons that become apparent when the invention is fully described, an object of the present invention is to provide an improved technique for determining the concentrations of fluids, both gaseous and liquid, in mixtures of more than two fluids in real time.

It is a further object of the present invention to minimize the cost of a fluid analysis apparatus by employing low-cost but accurate fluidic and/or non-fluidic sensor elements.

It is another object of the present invention to integrate a gas analysis device into the main gas flow passage of a breathing circuit.

It is another object of the present invention to incorporate a gas analyzer into a monitoring system in a manner that minimizes the overall cost, complexity and number of sensors of the system.

Another object of the present invention is to provide a direct quantitative measure of uptake, consumption and production of various inspired and respired gasses in real time.

It is yet a further object of the present invention that the fluid analyzer system operate with a minimum number of moving mechanical parts requiring little or no user calibration so that the entire process can operate virtually indefinitely.

It is still a further object of the present invention to provide a plurality of utilization modes ranging from permanent installations in operating rooms to portable home-use devices that can be used in residences or temporary situations.

It is another object of the present invention to convey gas concentration information in a manner conducive to easy readout and compatible with personal computers and other forms of microprocessors.

It is another object of the present invention to provide a method and apparatus for augmenting the gas analysis capabilities of conventional gas analyzers using low-cost, reliable devices, whereby concentrations of a greater number of gasses, including gasses whose concentrations are difficult to determine by conventional means, can be determined.

Yet another object of the present invention is to provide for a universal sensing mechanism which is independent of the gasses being analyzed, use specificity of the analysis being provided only by changes in parameters provided to the analysis software by the user.

Still another object of the present invention is to provide for a means of determining gas concentrations entirely from first physical principles, thereby resulting in a system that never requires calibration or adjustment.

A still further object of the present invention is to extend the fluid analysis principles of the aforementioned Drzewiecki patent application to mixtures of greater numbers of fluids.

The aforesaid objects are achieved individually and in combination, and it is not intended that the present invention be construed as requiring two or more of the objects to be combined unless expressly required by the claims attached hereto.

In accordance with the present invention, there is disclosed an improved mainstream implementation of the system described in the aforementioned Drzewiecki patent application, which has a further advantage that it can be directly incorporated into a metabolic rate monitoring system by virtue of the fact that the measurement of the tidal flow, the mainstream flow through the sensor, with the derived concentrations, provides a direct quantitative measure of uptake, consumption and production of various gasses.

One preferred implementation of such a device includes a low-cost pressure-drop flow element, the pressure drop across which is related to the flow rate, density and viscosity of the tidal flow gas mixture. The device further includes a pair of piezo-electric (or other) acoustic (sonic or ultrasonic) sources disposed axially a fixed distance apart along the flow direction coupled with acoustic sensors (microphones, piezo-electric film, etc.) in a fashion commonly found in ultrasonic flowmeters. The propagation time for an acoustic transmission between the upstream source and the downstream sensor is due to the speed of sound plus the stream velocity along the flow axis (the acoustic signal travels with the flow). The propagation time for an acoustic transmission between the downstream source and the upstream sensor is due to the speed of sound minus the stream velocity in the opposite direction. The difference of these propagation times cancels the speed of sound and yields the flow velocity, which, coupled with the known fixed area of the mainstream orifice, gives flowrate. The sum of the propagation times cancels the flow velocity and leaves only the acoustic velocity (speed of sound) from which, with density, the specific heat of the gas may be derived.

A surface acoustic wave (SAW) device located in the stream, and operating at megahertz frequencies, can be used to determine the viscosity of the gas, as the surface acoustic wave is dominated by viscous effect in a well-known manner. From the measured flow element pressure drop, viscosity and flow rate the density can be determined. Combined with speed of sound from which specific heat is determined together with measurements of ambient pressure and temperature, the three equations relating constituent concentrations independent properties of the mixture (density, viscosity and specific heat) can be formed. The constitutive equation, requiring the sum of the constituent concentrations to equal unity, provides a fourth independent equation.

Furthermore, by allowing the gas mixture flow to pass between the electrically charged, substantially parallel plates of a suitable capacitor, the dielectric constant of the gas can be determined by measuring the capacitance of the capacitor. The dielectric constant of a gas mixture is related to the dielectric constants of the constituents by a simple dilution equation; that is, the dielectric constant of the mixture as a whole is equal to the volumetrically weighted sum of the constituent dielectric constants, or simply, the sum of the products of the individual dielectric constants and their respective volume concentrations.

Therefore, the preferred embodiment of the fluidic analyzer of the present invention measures four properties allowing for assaying/analyzing gasses of five constituents. In addition, tidal flow (inhaled and exhaled volumetric flow) is determined, which, when multiplied by the individual volume concentrations and densities, yields the mass flow of each individual constituent gas allowing for a direct measure of uptake (absorption in the tissues, etc.) of non-metabolized gasses (nitrogen, nitrous oxide, halogenated agents), consumption of oxygen and production of carbon dioxide and water vapor.

The gas analyzer of the present invention can be extended to analyze gas mixtures of six constituents by additionally measuring the refractive index of the gas mixture and forming a sixth independent equation, which together with the other five equations can be solved for six gas concentrations.

In accordance with the exemplary embodiment of the present invention, the need for a vacuum pump has been eliminated, and, consequently, the sampled gas is not disturbed. The measurement of an additional independent property, dielectric constant (and/or refractive index), has been introduced, and a mechanism for measuring tidal flow (and, by integration, tidal volume) has been provided, thereby providing all the necessary inputs and measurements to determine metabolic rates as well as cardiac output, non-invasively.

The foregoing improvements conform to the fundamental design object of producing a low cost device. All of the sensing elements of the gas analyzer have been demonstrated to be inexpensive. The issue of cost as it relates to the accuracy and resolution provided by these sensors rests primarily on the ability to process the signals with sufficient dynamic range to achieve the overall concentration accuracies of the order of 0.1–0.5 volume %. By using the SAW device to measure viscosity, one pressure transducer has beer eliminated. The exemplary embodiment has a further advantage over the micro-fluidic implementation in that there are no very small critical geometries that must be fabricated.

The improved fluid analyzer system therefore includes a mainstream implementation of a multiple gas-property-sensing device utilizing improved property sensors, an additional property measurement, and tidal flow and volume quantification.

The above and still further objects, features and advantages of the present invention will become apparent upon consideration of the following definitions, descriptions and descriptive figures of specific embodiments thereof wherein like reference numerals in the various figures are utilized to designate like components. While these descriptions go into specific details of the invention, it should be understood that variations may and do exist and would be apparent to those skilled in the art based on the descriptions herein.

DESCRIPTION OF THE PREFERRED EMBODIMENTS

The following detailed explanations of FIGS. 1–6 and of the preferred embodiments reveal the method and apparatus of the present invention. In accordance with the present invention, there is disclosed an improved mainstream implementation of the system described in the aforementioned Drzewiecki patent application, which has a further advantage that it can be directly incorporated into a metabolic rate monitoring system by virtue of the fact that the measurement of the tidal flow, the mainstream flow through the sensor, with the derived concentrations, provides a direct quantitative measure of uptake, consumption and production of various gasses.

Although the following description is primarily concerned with medical gas analyzers, the present invention is not limited to the preferred embodiment but is applicable to other gas analysis applications, including, but not limited to, industrial production of gasses, atmospheric analysis, pollution tracking and other applications for the detection and analysis of chemical and biological agents. In addition, the present invention is not limited to a specific number of gasses that are in a mixture or for that matter only fluidic sensors, but rather, since properties of gasses can be measured using a variety of low cost electronic and hybrid electro-fluidic devices, the present invention may extend to low cost scientific gas analysis of large numbers of gasses. Furthermore, the present invention is not limited to the analysis of only gasses, because it should be recognized that substantially the same methods and apparatus may be applied to the analysis of mixtures of liquid fluids as well, provided sufficient differences in mixture properties occur due to the changes of concentrations of the constituents of the fluids.

In accordance with the present invention, individual concentrations of fluid constituents of a mixture of N known fluids are determined by measuring characteristics of the mixture flowing through a number of sensing devices, determining N−1 properties of the mixture from the measured characteristics, establishing N−1 equations relating the individual concentrations of the fluid constituents to the N−1 properties of the mixture, and solving the N−1 equations and a constitutive equation in real time for the individual concentrations of the fluid constituents.

Figure 1:
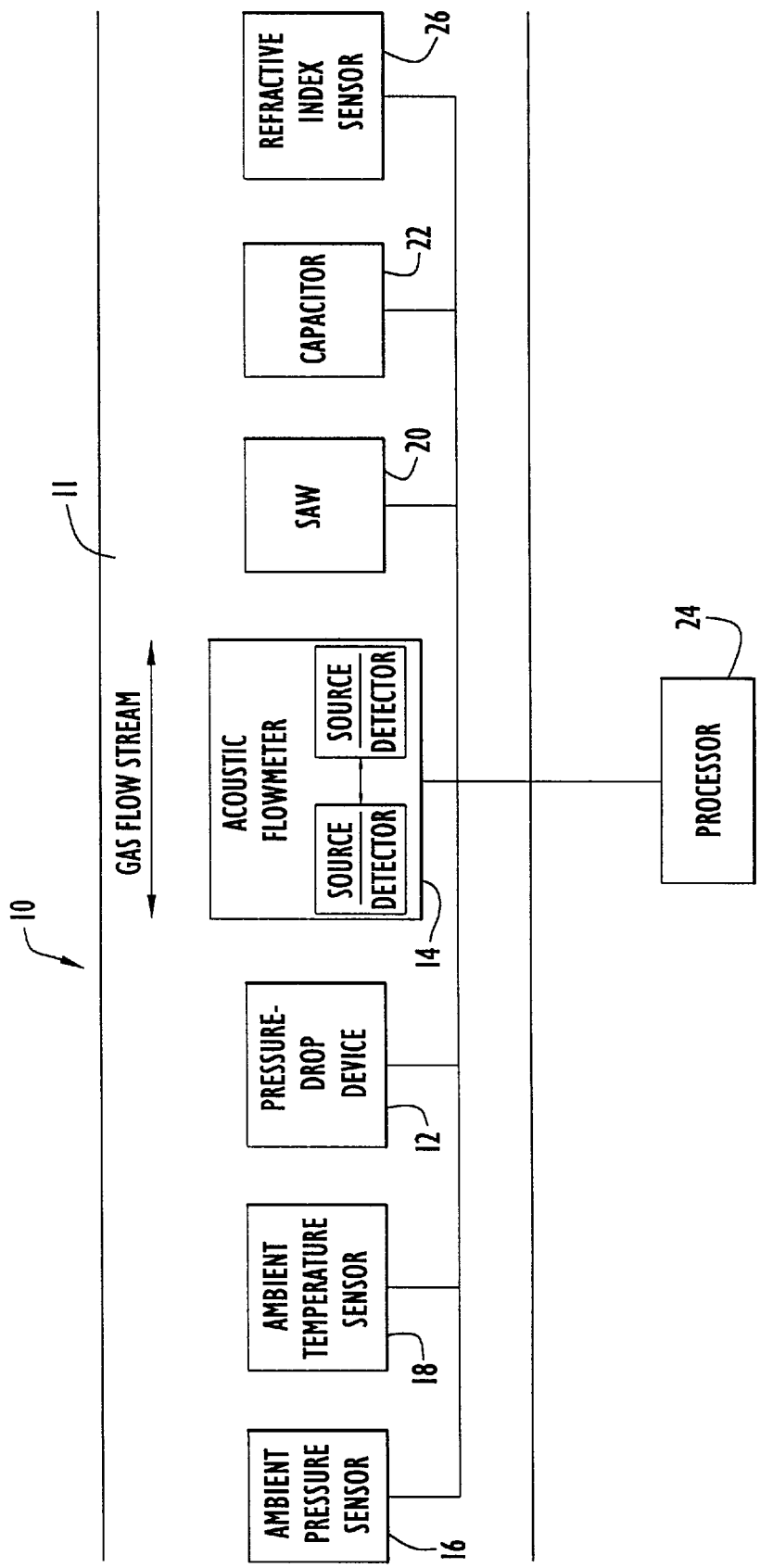
FIG. 1 is a schematic representation of a fluid analyzer in accordance with a first embodiment of the present invention.
Figure 2:
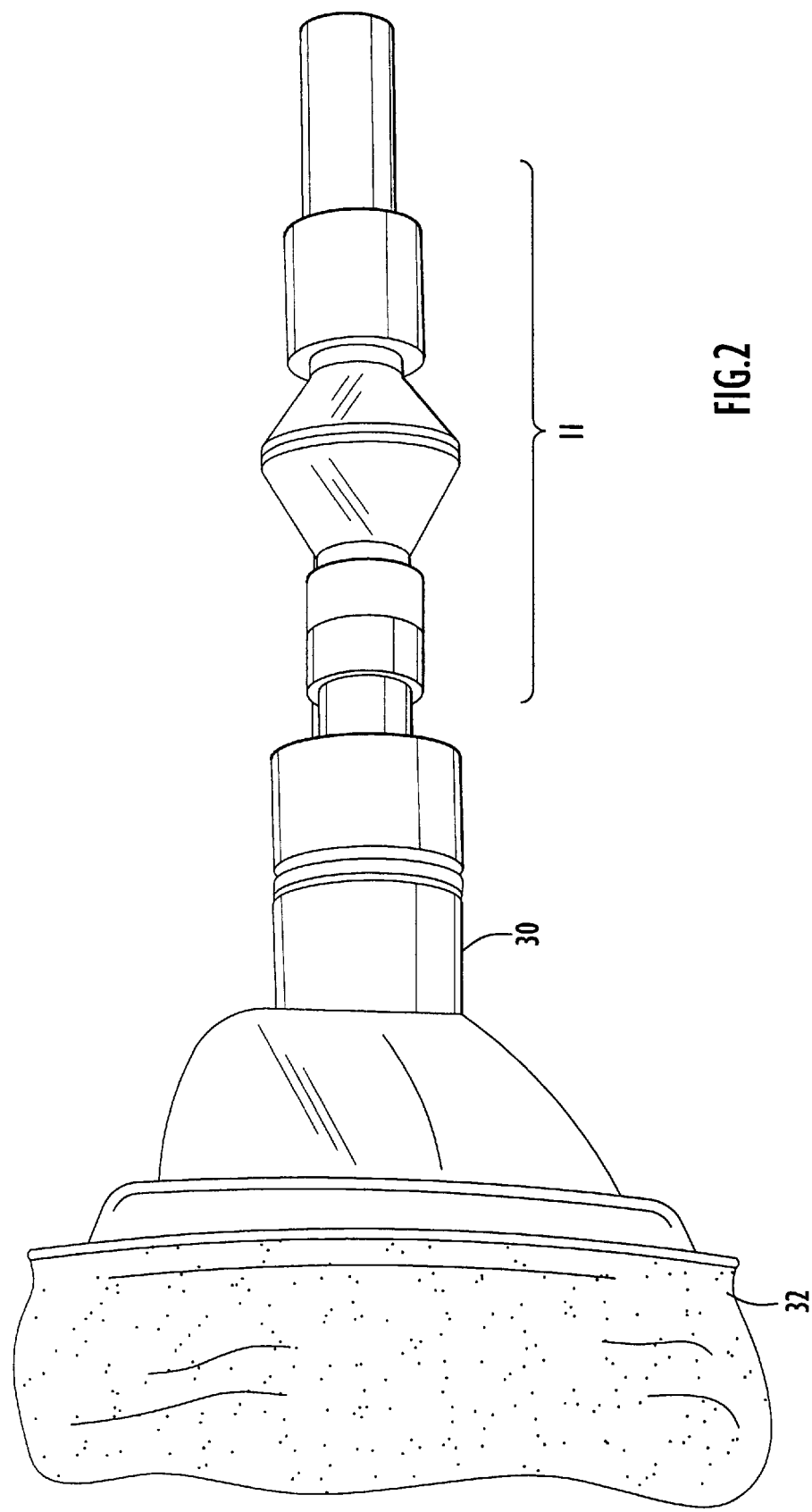
FIG. 2 is a graph showing the Hamilton respiratory flow element pressure-flow relationship as a function of density for $O_2$, $N_2$, and $CO_2$.

FIG. 1 is a schematic representation of a real time gas analyzer 10 in accordance with an exemplary embodiment of the present invention. In this exemplary embodiment, gas analyzer 10 is preferably incorporated into a main passageway 11 of a breathing circuit through which inhaled and exhaled gasses flow. As illustrated in FIG. 2, passageway 11 can be coupled via a humivent 30 to a face mask 32 positioned over the nose and mouth of a subject (not shown). Face mask 32 directs respired gasses from the subject into passageway 11 and directs gasses supplied through passageway 11 to the subject.

Referring to FIG. 1, gas analyzer 10 includes a low cost pressure-drop-type (fixed or variable orifice) flow element device 12 (e.g., a Venturi-type flowmeter, a bi-directional Hamilton variable area orifice device or a variable flap orifice), the pressure drop ($\Delta P$) across which is related in a known manner to the flowrate (Q) and the gas density ($\rho$) and viscosity ($\mu$). While device 12 can be a flowmeter or other pressure-drop device, it should be understood that device 12 is not used to measure the gas flow rate in gas analyzer 10. Rather, the measured pressure drop is used in determining the gas mixture density; thus, device 12 essentially functions as an orifice or densitometer. The pressure drop and flow rate through a fixed (nozzle, venturi) or variable (rotometer, flap) orifice depends primarily on the density of the gas mixture, as noted in the Bernoulli orifice equation, $$\Delta P = \rho Q^2 / (c_d^2 A^2) \quad (1)$$

where $\Delta P$ is the pressure drop, $\rho$ is the density, Q is the volumetric flow, $c_d$ is the discharge coefficient (which typically is viscosity dependent) and A is the cross-sectional area.

Figure 3:
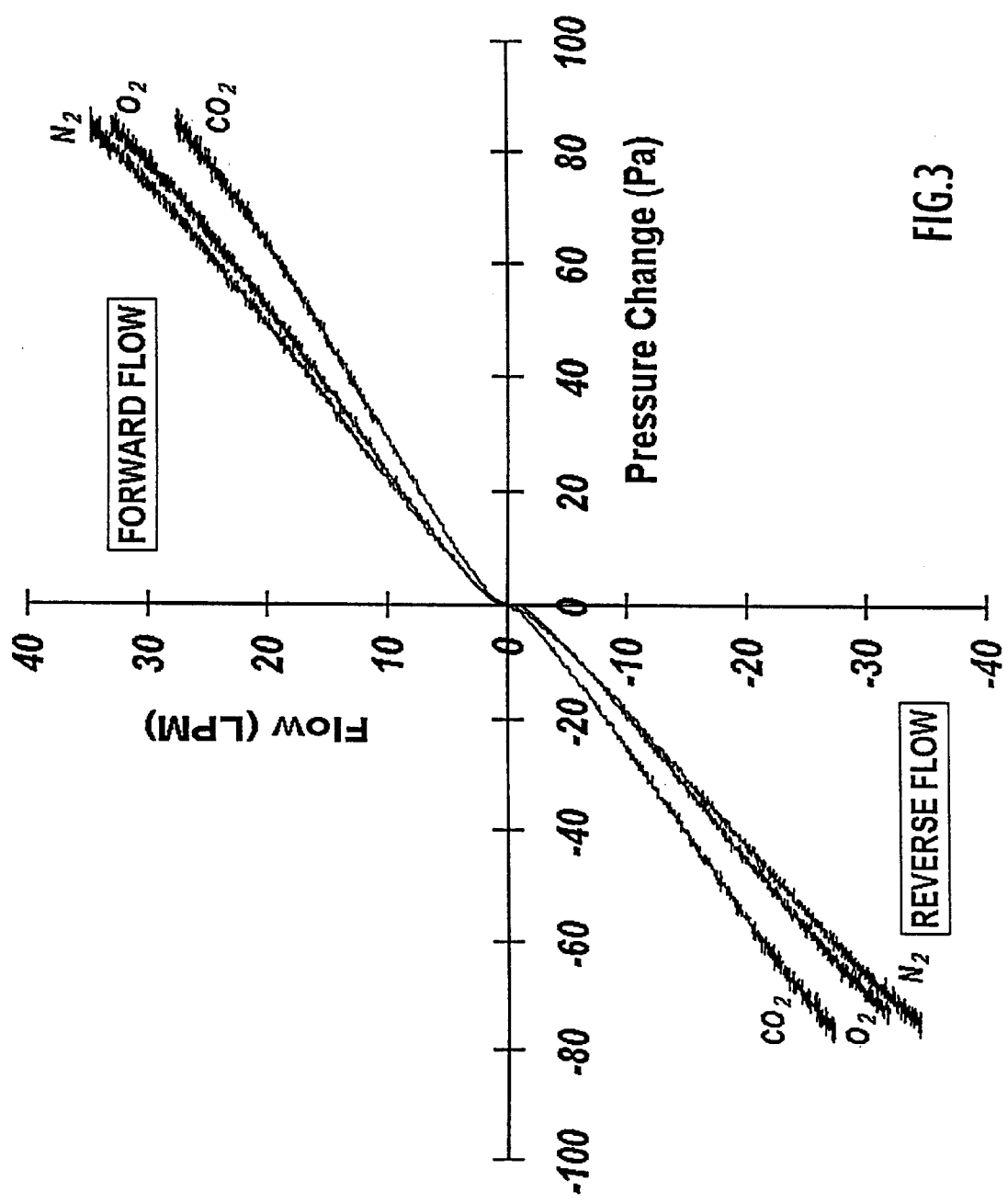
FIG. 3 is perspective view of a portion of a breathing circuit into which the gas analyzer of an exemplary embodiment of the present invention is incorporated.

The pressure-flow relationship for a very low cost bi-directional Hamilton variable area orifice device for the three constituent gasses in air (nitrogen, oxygen, and carbon dioxide), is shown in FIG. 3, which clearly demonstrates the device's density dependence (e.g., high density $CO_2$ has lowest flow at the same pressure drop) and the error incurred if density is unknown. The pressure-flow relationship for this device, where the area is a function of the pressure drop via the displacement of a wedge-shaped flap can be shown to be:

$$Q^2 = [L^2 / 2A_F^2 k^2 \rho][\Delta P^3 - \Delta P^5 / 4A_F^2 k^2 L^2] \quad (2)$$

where L is the characteristic dimension of the flap, $A_F$ is the area of the moving flap and k is the effective spring constant of the cantilevered flap, and $\rho$, again, is the density.

The flow element pressure drop ($\Delta P$) can be measured by any number of state-of-the-art electronic pressure transducers, e.g., a low-cost, integrated circuit (IC) semiconductor strain gage pressure transducer (MEMS-based). Referring to equation (1), once the pressure drop ($\Delta P$) has been measured, the remaining unknown variables are the density ($\rho$) of the gas mixture, the volumetric flow rate Q, and the viscosity ($\mu$) of the gas mixture (related to the discharge coefficient $c_d$). Thus, by independently determining the flowrate Q and viscosity ($\mu$) of the gas mixture, the density ($\rho$) of the gas mixture can be determined from equation (1).

To that end, gas analyzer 10 further includes an acoustic flowmeter 14 having a pair of piezo-electric (or other) sonic or ultrasonic sources disposed axially a fixed distance apart along the direction of the gas flow stream. The sources are respectively coupled to acoustic sensors (e.g., microphones, piezo-electric film, etc.) in a fashion commnonly found in, for example, ultrasonic flowmreters. The upstream source transmits an acoustic (sonic or ultrasonic) wave that travels downstream along the flow axis (i.e., in the same direction as the gas flow stream) and is detected by the downstream sensor. The acoustic sensor measures the propagation time ($\Delta T_{Downstream}$) required for the acoustic wave to travel from the upstream source to the downstream source/sensor, and the velocity of the downstream-traveling wave ($V_{Downstream}$) can be determined directly from the downstream propagation time. The velocity of the downstream-traveling wave ($V_{Downstream}$) is equal to the sum of the speed of sound (a) in the mixture and the gas stream velocity ($V_{Downstream} = a + V$), since the downstream-traveling acoustic wave travels in the same direction as the gas stream.

Similarly, the downstream source transmits an acoustic wave that travels upstream along the flow axis (i.e., in the opposite direction as the gas flow stream) and is detected by the upstream sensor. The acoustic sensor measures the propagation time ($\Delta T_{Upstream}$) required for the acoustic wave to travel from the downstream source to the upstream source/sensor, and the velocity of the upstream-traveling wave ($V_{Upstream}$) can be determined directly from the upstream propagation time. The velocity of the upstream-traveling wave ($V_{Upstream}$) is equal to the difference of the speed of sound (a) in the mixture and the gas stream velocity ($V_{Upstream} = a − V$), since the upstream-traveling acoustic wave travels in the opposite direction as the gas stream.

By taking the difference of the upstream and downstream propagation times ($\Delta T_{Upstream} − \Delta T_{Dowstream}$), the propagation time due to the speed of sound is eliminated, and this time difference directly yields the gas velocity V:

$$V = 2(\text{distance between the sources})/(\Delta T_{Upstream} - \Delta T_{Downstream}), \quad (3)$$

where V=Q/A, Q is the flow rate and A is the cross-sectional area of the channel.

Referring once again to equation (1), having independently determined the flow rate Q, the remaining unknowns are the density ($\rho$) of the gas mixture and the discharge coefficient ($c_d$), which is dependent on the viscosity ($\mu$) of the gas mixture. Additionally, since the cross-sectional area of the mainstream orifice transverse to the flow direction is known, knowledge of the flow rate Q can be used to determine the tidal flow rate and, with time integration, the tidal flow volume.

Similarly, by taking the sum of the upstream and downstream propagation times ($\Delta T_{Upstream} + \Delta T_{Downstream}$), the propagation time due to the gas flow rate is eliminated, leaving a sum attributable only to acoustic velocity (a) (i.e., speed of sound in the mixture), from which the specific heat of the gas may be derived.

$$a = 2(\text{distance between the sources})/(\Delta T_{Upstream} + \Delta T_{Downsteam}) \quad (4)$$

The specific heat at constant pressure, $c_p$, is a unique gas property independent of density and viscosity and can be determined from the speed of sound (a) in the gas mixture. From the kinetic theory of gasses, the speed of sound, a, is defined as:

$$a = [\gamma_{mix} R_o T/M_{mix}]^{1/2}, \text{ or } \gamma_{mix} = a^2 M_{mix}/R_o T \quad (5)$$

where $R_o$ is the universal gas constant, T is the absolute temperature, $M_{mix}$ is the molecular weight of the gas mixture and $\gamma_{mix}$ is the ratio of specific heats, $c_p/c_v$ of the gas mixture, $c_v$ being the specific heat at a constant volume. Molecular weight is directly proportional to density. The specific heats $c_p$ and $c_v$ are related by the gas constant and molecular weight:

$$c_p = c_v + (R_o/M) \quad (6)$$

From equations (5) and (6), the following expression for $c_p$ can be derived:

$$c_p = 1/[(M/R_o) - (T/a^2)] \quad (7)$$

Since density $\rho$ is related to molecular weight M and absolute pressure $P_{amb}$ (terms that are measured), equation (7) can be rewritten as:

$$c_p = 1/[T(\rho_{mix}/P_{amb} - 1/a^2)] \quad (8)$$

Gas analyzer 10 includes a pressure sensor 16 that measures the ambient absolute pressure ($P_{amb}$) of the gas mixture and a temperature sensor 18 that measure the ambient gas temperature (T) required by equation (8). The temperature sensor 18 can be a simple, ultra low cost electronic temperature sensor, such as Analog Devices AD590 device to provide the required accurate temperature input to the computational processor.

Referring again to FIG. 1, gas analyzer further includes a surface acoustic wave (SAW) device 20, operating at a frequency of many megahertz, and located in the gas flow stream. SAW 20 can be used to determine the viscosity ($\mu$) of the gas mixture, as the surface acoustic wave is dominated by viscous effect in a well-known manner. Specifically, by measuring the resonant characteristic of the SAW as the gas mixture traverses its surface, the viscosity of the gas mixture can be readily determined. Having independently measured the viscosity ($\mu$) of the mixture (which allows the discharge coefficient $c_d$ to be determined), the orifice pressure drop ($\Delta P$), and the volumetric flow rate Q, the density ($\rho$) of the gas mixture can be readily determined from equation (1). Thus, the suite of sensors comprising the pressure-drop device 12, the acoustic flowmeter 14, the SAW device 20, together with the absolute pressure and temperature sensors 16 and 18, allows the independent properties of density ($\rho$), viscosity ($\mu$) and specific heat ($\gamma$) of the gas mixture to be determined, together with the end-tidal volumetric flow rate Q.

Referring once again to FIG. 1, gas analyzer 10 further includes a capacitor 22 having electrically charged, substantially parallel plates (or electrodes) arranged to permit the stream of gas to pass between the plates. As the gas mixture flows between the electrically charged plates, the capacitance of the capacitor varies in accordance with the dielectric constant ($\kappa$) of the gas mixture. Consequently, the dielectric constant ($\kappa$) of the gas mixture can be determined by measuring the capacitance (or relative change in capacitance) of the plates or electrodes as the gas mixture passes between the plates.

The dielectric constant ($\kappa$) of the gas mixture represents a fourth independent property, together with density ($\rho$), viscosity ($\mu$) and specific heat ($\gamma$). These four properties can be used to determine the concentrations of the individual constituents of a mixture of five gasses by applying the technique disclosed in the aforementioned Drzewiecki patent application. More specifically, the five unknown constituent concentrations can be determined by solving five equations relating properties of the mixture as a whole to the five unknown concentrations. The equations from which the constitute gas volume concentrations are determined are formulated as described in the following paragraphs.

The density of a mixture of gasses, $\rho_{mix}$, is equal to the sum of the products of the concentrations, $C_i$, and the specific densities, $\rho_i$, of the N constituents as determined by applying the law of conservation of matter:

$$\rho mix = \Sigma \rho_i C_i, i=1 \text{ to } N. \quad (9)$$

The viscosity of a gas mixture is related to the concentrations of the individual gas components, as determined from the principles of the kinetic the cry of gasses, and as shown by the relationship between mixture viscosity and individual concentrations (see Golubev, "Viscosities of Gasses and Mixtures", NTIS Doc. TT70-50022, 1970, incorporated herein by reference in its entirety), which relationship is given by:

$$\mu_{mix} = \Sigma[C_i \mu_i/[C_i + \Sigma C_j \Phi_{ij}]]; i=1, \ldots, k; j \neq i \quad (10)$$

where $$\Phi_{ij} = [1 + (\mu_i/\mu_j)(M_j/M_i)^{1/4}]^2/2.828[1 + M_i/M_j]^{1/2},$$

k is the number of constituents, and $M_i$ is the known molecular weight of the ith component of the mixture.

The relationship between the concentrations of the various gasses and the specific heat is a similarly simple linear relationship. The specific heats of the mixture are related to the individual component specific heats by weight fraction of each component; thus, $$c_{p\ mix} = \Sigma C_i M_i c_{pi}, i=1 \text{ to } N \quad (11)$$

and $$c_{v\ mix} = \Sigma C_i M_i c_{vi}, i=1 \text{ to } N \quad (12)$$

Either one (but not both) of equations (11) and (12) can serve as one of the equations used to calculate the constituent concentrations.

The dielectric constant of a gas mixture ($\kappa_{mix}$) is related to the dielectric constants of the N constituents by a simple dilution equation; that is, the mixture dielectric constant is equal to the volumetrically weighted sum of the constituent constants, or simply, the sum of the products of the individual dielectric constants and their respective volume concentrations, in exactly the same formulation use to describe the density.

$$\kappa mix = \Sigma \kappa_i C_i, i=1 \text{ to } N \quad (13)$$

If a five gas mixtures is of interest, the fifth equation relating the constituent concentrations is the constitutive equation, which states that the sum of the volume concentrations of all of the gasses must equal unity, $$\Sigma C_i = 1. \tag{14}$$

The resulting system of five algebraic equations (equations (9), (10), (13), (14) and one of (11) and (12)) can be uniquely solved, in real-time, for the individual concentrations, $C_i$. A microprocessor 24 (FIG. 1), or other computational mechanism (e.g., a personal computer, etc.) can be readily programmed to solve this set of equations. The resultant concentrations may be plotted in real time on a computer CRT or LCD screen in multiple colors in separate traces, or in any other convenient manner. For example, microprocessor 24 can drive a display (not shown), such as a CRT which continuously may display the concentrations of any or all of the three gasses as well as providing any desired numeric outputs, such as respiration rate, numeric values of concentrations, as well as any limits. Use of electronics: with memory provides for recall of previous data for comparison. Also, the microprocessor may be programmed to provide visual and aural alarms in the event of particular occurrences such as overdosing, poor metabolization of oxygen, low or high respiration rates and any other functions as may be desired.

Figure 4:
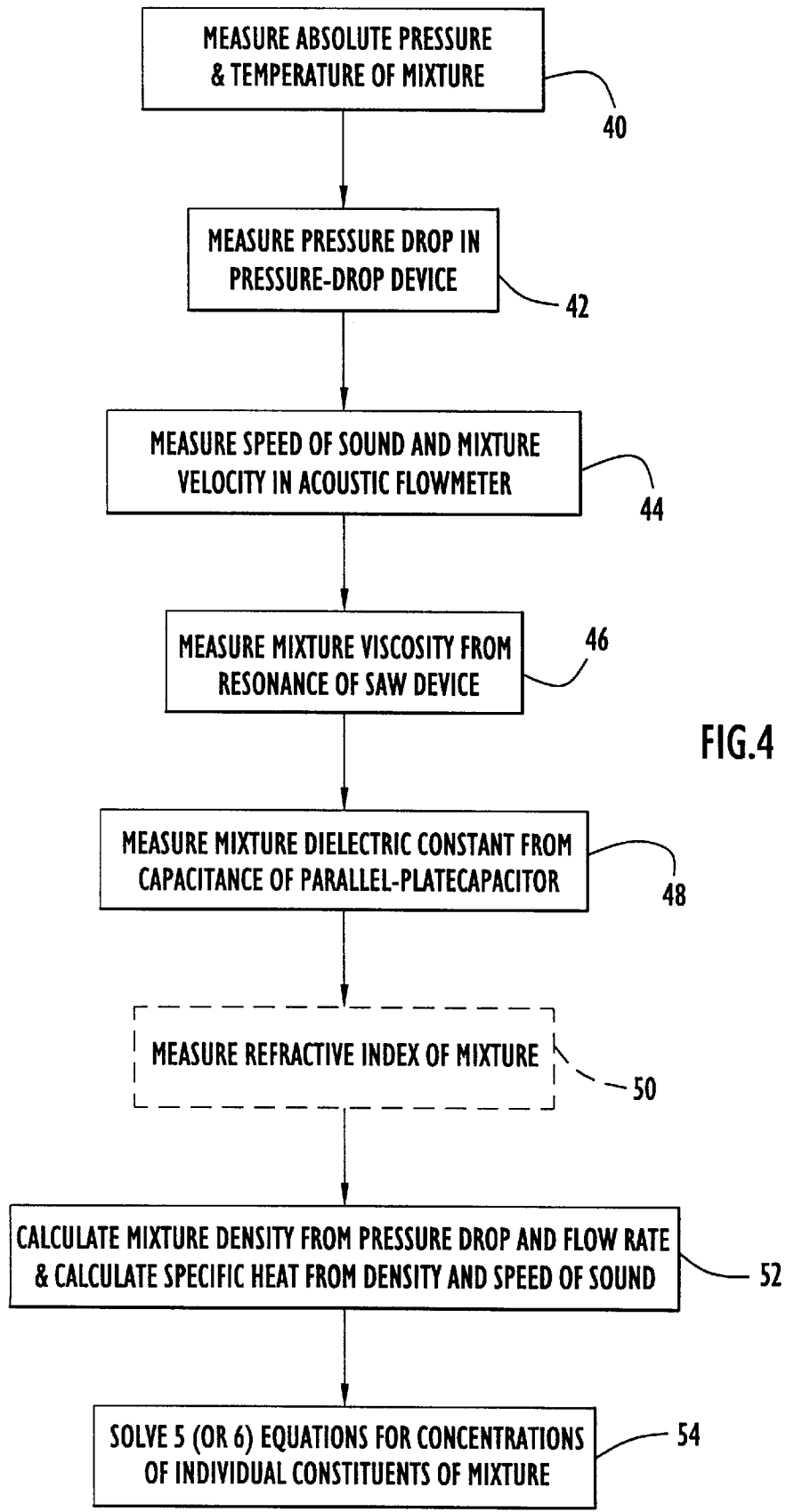
FIG. 4 is a flow chart summarizing the processing steps involved in determining the individual concentrations of the constituent gasses of a mixture of gasses.

Thus, in accordance with the above-described exemplary embodiment of the fluidic analyzer of the present invention, four independent properties of a mixture of gasses are measured, allowing for assaying/analyzing gasses of five constituents. FIG. 4 is a flow chart summarizing the above-described processing steps (steps 40, 42, 44, 46, 48, 52 and 54) involved in determining the individual concentrations of the constituent gasses in a mixture of five known gasses. In addition, tidal flow (inhaled and exhaled volumetric flow Q) is determined, which, when multiplied by the individual volume concentrations and densities, yields the mass flow of each individual constituent gas allowing for a direct measure of uptake (absorption in the tissues, etc.) of non-metabolized gasses (nitrogen, nitrous oxide, halogenated agents), consumption of oxygen and production of carbon dioxide and water vapor. These measurements can be used by a monitoring system, such as a non-invasive cardiac output monitor, to determine cardiac output, pulmonary function and metabolic rate information. For example, the gas analyzer of the exemplary embodiment can be incorporated into an improved implementation of the cardiac output monitoring system described in the aforementioned Calkins patent application.

Further, in accordance with this exemplary embodiment of the present invention, the need for a vacuum pump has been eliminated; consequently, the sampled gas is not disturbed. The measurement of an additional independent property, dielectric constant, has been introduced, and a mechanism for measuring tidal flow (and, by integration, tidal volume) has been provided, thereby providing all the necessary inputs and measurements to determine metabolic rates as well as cardiac output, non-invasively.

The foregoing improvements conform to the fundamental design object of producing a low cost device. All of the sensing elements described have been demonstrated to be inexpensive. The issue of cost as it relates to the accuracy and resolution provided by these sensors rests primarily on the ability to process the signals with sufficient dynamic range to achieve the overall concentration accuracies of the order of 0.1–0.5 volume %. By using the SAW device to measure viscosity, one pressure transducer has been eliminated. This embodiment has a further advantage over the micro-fluidic implementation in that there are no very small critical geometries that have to be fabricated.

The improved fluid analyzer system therefore includes a mainstream implementation of a multiple gas-property-sensing device utilizing improved property sensors, an additional property measurement, and tidal flow and volume quantification.

It will be understood that the principles of the present invention can be extended to analyze mixtures of greater numbers of gasses, provided additional independent properties of the mixture can be accurately measured and related to the concentrations of the gas constituents. As briefly suggested in the Drzewiecki patent application, the refractive index (n) of the mixture can serve this purpose, extending the above-described five-gas analyzer to a six-gas analyzer. Referring to FIG. 1, a refractive index sensor 26 can be incorporated into gas analyzer 10 in passageway 11. The refractive index (n) of a medium (e.g., a gas mixture) is equal to the ratio of the speed of light in a vacuum to the speed of light in the medium. Using modern laser and optical technology, any of a variety of simple techniques can be implemented to measure refractive index (step 50, FIG. 4) with sufficient accuracy to deconvolve the simultaneous equations to obtain a mixture assay. For example, the beat frequency between two transmitted light signals, one through a vacuum and one through the gas mixture, can be used to determine the relative light velocities and hence refractive index.

As with the dielectric constant, the refractive index of a gas mixture ($n_{mix}$) is related to the refractive indices of the N constituents by a simple dilution equation; that is, the mixture refractive index is equal to the volumetrically weighted sum of the constituent refractive indices, or simply, the sum of the products of the individual refractive indices and their respective volume concentrations.

$$n_{mix} \Sigma n_i C_i, \, i=1 \text{ to } N \tag{15}$$

The resulting system of six algebraic equations (equations (9), (10), (13), (14), (15) and one of (11) and (12)) can be uniquely solved, in real-time, for the individual concentrations ($C_i$) of six constituent gasses in a mixture. Six-gas mixtures occur in anesthesia administration when water vapor is not removed, or when air is used as the anesthesia carrier. Air additionally introduces argon at about one percent concentration to the gas mixture. The presence of the inert gas argon, however, may be treated as a known constant concentration, in which case properties need be measured. The other trace gasses are in such small concentrations that they do not materially affect the bulk properties of the overall mixture to a discernable amount within the desired clinical accuracy of the system. Water vapor normally occurs at 100% humidity, if not desiccated, and under certain circumstances may also be treated as a known fixed constituent. Removal of water vapor is desirous, however, as it may condense in the fluid passages thereby changing the fluid resistance properties and thus affecting output readings. Operation of the system at elevated temperature to avoid condensation would require a separate heater which, from an energy consumption stand point, is not desirable.

The gas analyzer of the present invention may be utilized in various locations, such as the home within a home therapy device, or ambulances and other locations experiencing field trauma within an emergency medicine device for validating ventilation and checking for proper intubation of a patient. The gas analyzer may be used with ventilalor-dependent patients, patients with respiratory insufficiencies or patients having or suspected of having a compromised respiratory system wherein the monitor may be used in various locations, such as ambulances, hospitals and/or sub-acute care facilities, and during patient transport between these facilities. Further the gas analyzer of the present invention can be used in operating rooms, outpatient surgery centers or any facility that uses anesthetic gasses and/or sedation to monitor anesthesia gas administration by analyzing concentrations of multiple respired anesthetic gasses simultaneously.

In the context of anesthesia gas administration, determination of the concentrations of an additional gas can be achieved without measuring an additional independent property by adding an additional piece of information to solve for the additional gas. Mixtures of five or more gasses typify modern anesthesia administration. The five gasses are typically: nitrogen, oxygen, carbon dioxide, nitrous oxide, and a potent, volatile anesthetic agent. Additional gasses may include water vapor, helium (used in laser surgery) or a second volatile anesthetic agent. Nitrogen is the primary component of air and is typically present in respired gasses, and even when the administered gasses are free of nitrogen (which is typically the case during administration of anesthesia) nitrogen remains present as a residual for several minutes from previously having breathed air. The ability to measure nitrogen is a major safety benefit during administration of anesthesia, since a sudden small presence of nitrogen may indicate an air embolism, and a large presence may indicate a loss of breathing circuit integrity (e.g., a leak in the system).

Measurement of the concentration of oxygen, which is administered or present in air, provides redundancy to the breathing circuit $O_2$ sensor (e.g., a Clark electrode) and eliminates any pulse oximeter CO ambiguity. Measurement of the concentration of $CO_2$, which is a product of the body's metabolic processes, can be combined with the oxygen measurement to provide a respiratory quotient and to validate respiration.

Nitrous oxide is typically administered in combination with a volatile anesthetic agent, and measurement of its concentration prevents overdosing and asphyxiation. Volatile halogenated anesthetic agents are administered to induce anesthesia and include: halothane, desflurane, sevoflurane, enflurane, and isoflurane.

Importantly, however, carbon dioxide and nitrous oxide have almost exactly the same molecular weight, density and viscosity and very similar specific heats. Thus, these two gasses, typically present in respired anesthesia gasses, cannot easily be distinguished by these properties. Given sufficient pressure transducer and flow sensor resolution, these two gasses can be resolved; however, from a practical aspect, resolution would have to be improved by an order of magnitude from the current state-of-the-art. However, anesthesia machines typically remove carbon dioxide from the stream of air that is inspired by the patient under anesthesia; thus, the concentration of carbon dioxide in the inspired gasses is known to be zero. This fact can be used to extend the capabilities of an N gas analyzer to determine the concentrations of N+1 gasses in a typical mixture of anesthesia gasses.

Specifically, for purposes of solving the above-described five (or six, with refractive index) equations relating properties of the mixture to individual gas concentrations, carbon dioxide and nitrous oxide are considered to be a single gas, and it is assumed that their properties cannot be distinguished and are the same. Thus, for example, equations (9), (10), (13), (14) and one of (11) and (12) are solved for the concentrations of oxygen, nitrogen, two different potent anesthetic gasses, and the combination of carbon dioxide and nitrous oxide. The individual concentrations of nitrous oxide and carbon dioxide can then be determined in the following manner. The combined concentration of nitrous oxide and carbon dioxide varies cyclically with respiration, as the concentration of carbon dioxide varies from near zero in the inspired gasses to a maximum during exhalation. Thus, the minimum combined concentration in each cycle can be assumed to be the concentration of nitrous oxide, while the concentration of carbon dioxide can be assumed to be the difference between the combined carbon dioxide-nitrous oxide concentration (which is varying throughout each respiration cycle) and the most recent minimum combined concentration (i.e., the nitrous oxide concentration). According to this approach, the carbon dioxide concentration is computed and updated throughout each cycle (as is the concentration of oxygen, nitrogen and the anesthetic agent), while the nitrous oxide concentration is updated once during each respiration cycle.

Using the assumption that carbon dioxide and nitrous oxide are a single constituent, the steps shown in FIG. 4 are carried out to determine the concentrations of five gas constituents by solving five simultaneous equations. Subsequently, the individual concentrations of carbon dioxide and nitrous oxide are determined in the previously-described manner.

In accordance with another aspect of the present invention, where the relative ratio of certain constituents in a gas or fluid mixture remain constant over time, these constituents can be treated as a single gas (fluid) in solving for the concentrations of the other constituents. For example, in an industrial application, it may be desirable to measure the concentrations of a number of generated gasses that are exhausted into the air. Naturally, as the generated gasses mix with air, the concentration of the air in the mixture will vary with the concentration of the generated gasses. However, assuming that none of the generated gasses consumes any of the components of air, the ratio of concentrations of the constituents of air will not vary over time (e.g., the proportion of oxygen to nitrogen within the air does not vary). Consequently, all of the constituents of air can be considered as a single pseudo-gas for purposes of determining the concentrations of the other generated gasses in accordance with the methodology of the present invention. That is, because the ratios of the components of air do not vary over time, the properties of "air" (density, viscosity, specific heat, dielectric constant and refractive index) remain fixed and known, and can be used in the foregoing equations in a manner as if air was a single gas. More generally, in any circumstance where the relative concentrations of plural gasses (fluids) are known and fixed over time, these gasses can be treated as a single pseudo gas constituent, and the individual concentrations of gasses so grouped can be determined by measuring the concentration of the pseudo gas and subsequently computing the individual constituent concentrations from the known ratios of the constituents. In this manner, the number of sensors required to determine the concentrations of the constituents of a mixture of gasses can be reduced in those applications where the concentration ratios of certain gasses do not vary, and/or the maximum number of mixture constituents that can be analyzed can be increased.

One of the important advantages of the present invention is the ability to simultaneously determine the individual concentrations of N gasses in a mixture of N known gasses by using inexpensive sensors to measure properties of the mixture as a whole and by solving N independent equations relating to the properties of the mixture. Although the above examples describe the invention with five to seven gasses, the invention is not limited to the determination of concentrations of any particular number of gasses. If additional properties of the mixture can be independently measured by any means and related to unknown concentrations, concentrations of additional gas constituents can be determined. In general, if N−1 independent properties of the mixture of gasses can be measured, then N equations can be developed and solved for N gas concentrations (the Nth equation being the constitutive equation).

Other independent thermodynamic properties include, but are not limited to: heats of formation and critical temperature. It should be noted that properties such as thermal conductivity are dependent on specific heat and viscosity and hence are not independent. Other physical properties such as absorptivity may also be useful.

Further, while fluidic measurement of the properties of a gas mixture offers a low-cost alternative to more expensive conventional sensors, the principles of the present invention can be extended to include any device that measures properties of the mixture as a whole or concentrations of individual gasses. For example, assume that a particular sensor is capable of determining the concentration of oxygen in a mixture of gasses. The information provided by this separate sensor (i.e., the oxygen concentration) is, in effect, an equation relating to a gas concentration, which equation can be used to solve other equations relating to gas concentrations. Thus, if the oxygen concentration measurement is supplied to the microprocessor along with the above-described measured properties, the concentration of an additional constituent of the gas mixture can be determined.

Importantly, the technique of the present invention can be used to determine the unknown gas concentrations in the mixture, regardless of what these gasses are, provided that the identity of the gasses is known and that each gas is distinguishable from all others by at least one of the measured properties. For example, it is desirable to be able to monitor the concentration of nitrogen in a mixture of exhaled gasses while a patient is being anesthetized. During the initial minutes during administration of anesthesia, nitrogen is present in the exhaled gasses, as nitrogen is liberated from lipids and fatty tissues. After approximately ten minutes, nitrogen is not normally present in a significant amount. A leak or break in a supply line would result in the continued presence of nitrogen in the exhaled gasses and can be detected by determining the concentration of nitrogen. However, nitrogen concentrations cannot be measured with conventional IR techniques; thus, more expensive techniques., such as mass spectroscopy typically have been required when it is desirous to determine nitrogen concentrations. According to the present invention, nitrogen concentration can be measured in a mixture of N gasses by measuring N−1 independent gas properties. Further, with the addition of M other sensors that respectively measure the concentrations of M individual gasses, the nitrogen concentration can be measured in a mixture of M+N gasses, where N−1 gas mixture properties have been measured. Thus, for example, measurement of four properties in accordance with the present invention can be combined with a conventional two-property measurement device to determine the concentration of seven gasses in a mixture (e.g. nitrogen, oxygen, water vapor, carbon dioxide, nitrous oxide and two anesthesia agents) in real time at very low cost.

More generally, in accordance with the present invention. the capabilities of an existing sensor system for measuring P gas concentrations can be extended to measure N additional gas concentrations by measuring N−1 properties of the gas mixture as a whole, regardless of what the gasses are, provided the identities of the gasses are known. Knowledge of the individual concentrations of certain gasses in the mixture reduces the number of unknowns; thus, N unknown individual concentrations in a mixture of N+P fluids can be determined by solving N equations, where individual concentrations of P fluids are known or determined by other means. For example, many existing anesthesia machines capable of measuring five gasses cannot measure the concentrations of nitrogen, carbon monoxide and helium. By augmenting such a five-gas monitor with the gas analyzer of the present invention, concentrations of these additional gasses can be measured with little additional expense.

Figure 5:
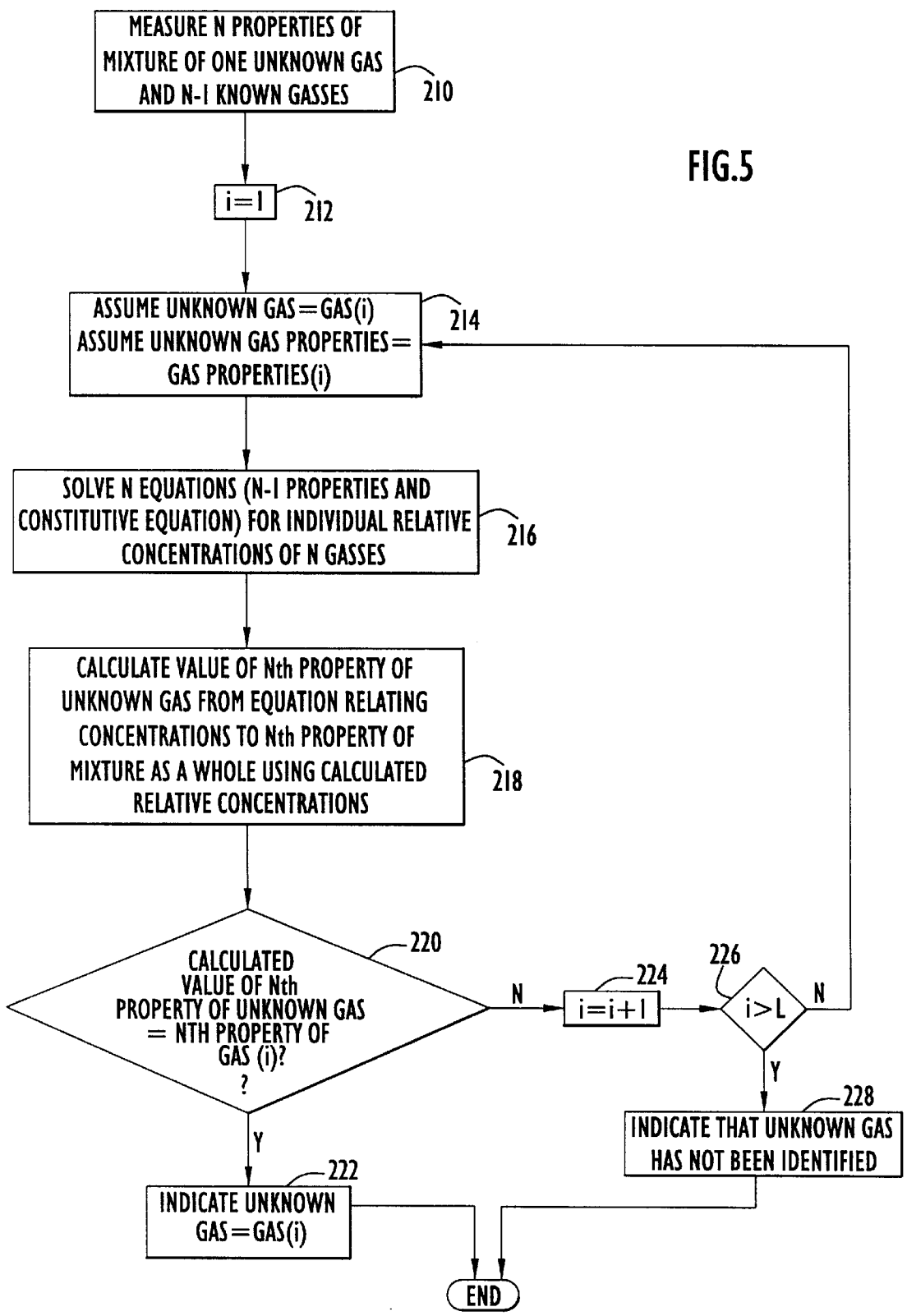
FIG. 5 is a functional flow diagram illustrating the processing steps required to determine the absolute identity of an unknown gas in a mixture of gasses in accordance with one embodiment of the present invention.

In general, in a mixture of N gasses in unknown concentrations, where the identities of N−1 gasses are known and the identity of one gas is unknown, the identity of the one unknown gas can be determined with an N+1 gas analyzer in accordance with the process summarized in the flow chart illustrated in FIG. 5. In a first step 210, N properties of the mixture are determined. For example, the density, viscosity, specific heat and dielectric constant of the mixture (N=4) as a whole can be determined using the above-described sensors. Further, concentrations of individual gasses can be determined using other, conventional sensors or other independently measured properties of the mixture as whole, which properties relate to relative concentrations. For example, the mixture could consist of four (N=4) gasses: oxygen, nitrogen, carbon dioxide and an anesthesia agent, where the anesthesia agent is assumed to be initially unknown. The four properties measured by a five-gas analyzer could be, for example: density, viscosity, specific heat and dielectric constant.

The unknown gas is then assumed to be one of a set of possible gasses. Specifically, a list of L gasses and their known properties are stored in a memory. For example, where the unknown gas is an anesthetic agent, a list of five or six anesthesia agents (e.g., halothane, enflurane, isoflurane, methoxyflurane, desflurane, sevoflurane) and their properties (e.g., density, viscosity, ratio of specific heats and dielectric constant) are stored in a look-up table in a memory. In step 212, a counter i, which indexes the look-up table, is initialized to a value of one, corresponding to a first anesthetic agent $A_1$ in the look-up table (i.e., the default agent, which can be, for example, anesthesia agent marked on the label of the container).

In step 214, the value of counter i (initially equal to one) is used to retrieve the name and properties of gas i in the look-up table, and the identity of the unknown gas is assigned (i.e., temporarily assumed to be) that of gas i, with the properties of the unknown gas being assigned the values of the properties of gas i retrieved from the look-up table. Initially, the value of i is set to one; thus, the unknown gas is assumed to be the default gas $A_1$ in the look-up table, and the properties of the unknown gas are assumed to be those of the default gas $A_1$.

In step 216, N−1 of the N properties are used to form N−1 equations relating to the relative concentrations, which, together with the constitutive equation (equation 6) are solved for the N relative concentrations of the N gasses in the mixture, using the assumption that the unknown gas has the properties of the gas $A_i$. For example, the equations for density, viscosity, specific heat and the constitutive equation can be used to calculate the relative concentrations of the oxygen, nitrogen, carbon dioxide and gas $A_i$. Note that the dielectric constant information (in this example) is not used in this step.

At this point, the only unknown in the equation which relates the Nth property of the mixture as a whole to the individual constituent concentrations is the Nth property of the unknown gas. Thus, in step 218, this equation can be solved for the Nth property of the unknown gas by inserting the calculated concentrations and the measured Nth property of the mixture as a whole (note that this equation was not used to determine the relative concentrations). For example, the dielectric constant of the unknown gas (assumed to be agent $A_i$ for purposes of computing concentrations) can be calculated from the dielectric viscosity equation (equation (13)) of the mixture and the computed concentrations of oxygen, nitrogen, carbon dioxide and gas $A_i$.

In step 220, the calculated $N^{th}$ property of the unknown gas is compared to the known (stored) $N^{th}$ property of gas $A_i$. If the value of the calculated property N of the unknown gas matches the value of (known) property N of gas $A_i$, it is determined that the unknown gas is gas $A_i$. In this case, it is indicated (on a display or the like) in step 222 that the unknown gas is gas $A_i$, and the identification process ends.

If the value of the calculated property N of the unknown gas does not match the value of (known) property N of gas $A_i$, it is determined that the unknown gas is not gas $A_i$. In this case, in step 224, the index counter i is incremented, and, in step 226, the index counter i is compared to the number L of gasses in the look-up table. If the index counter i is not greater than L, processing returns to step 214, and the process is repeated with the incremented value of i. If, on the other hand, the index counter i is determined to be greater than L in step 226, it is indicated in step 228 (on a display and/or by aural alarm) that the unknown gas has not been identified, and the identification process ends. Optionally, even where the identity of the gas is determined, an alarm (visual and/or aural) can be set off when the unknown gas is determined to be other than the default gas to indicate that the identity of the gas is other than the expected (default) gas.

Importantly, the above method of identifying an unknown constituent in a mixture can be carried out with the same hardware used to determine the concentrations of N known gasses. Only the processing software run on the signal processor is different. That is, to determine concentrations of known constituents, N−1 properties of the gas mixture are measured and N equations (including the constitutive equation) are solved for N unknown concentrations of N known constituents. In contrast, to identify an unknown constituent: N properties of the gas mixture are measured; N−1 of the properties are used to generate N−1 equations which, together with the constitutive equation, are solved for N concentrations, where the properties of the unknown constituent are assumed to be those of a particular gas; the N concentrations and the $N^{th}$ property of the mixture are used to calculate the $N^{th}$ property of the unknown gas which is then compared to the known Nth property of the gas assumed to be the unknown gas (for purposes of calculating the concentrations); and different gasses are tried (assumed to be the unknown gas) in this process until the comparison yields a match or all potential gasses have been tried without a successful match.

In general, in a mixture of fluids where concentrations of L fluids are unknown and identities of M fluids are unknown, the unknown concentrations and identities can be determined by measuring N−1 bulk properties of the mixture and by solving N equations (inclusive of the constitutive equation), where N=L+M (as used here, N does not necessarily represent the number of fluids in the mixture).

According to another embodiment of the present invention, the same hardware can be used to identify an unknown gas in a mixture of N gasses (including N−1 known gasses) using an N-gas analyzer measuring N−1 gas properties (i.e., by measuring one less property than in the gas identification method described above). This technique is particularly useful where the unknown gas is known to have a value of at least one property that is significantly different from the value of that property of the other gasses in the mixture. For example, the technique is suitable for identifying an anesthetic agent in a mixture of respired gasses, where the anesthetic agent has a significantly higher density than the other gasses.

Figure 6:
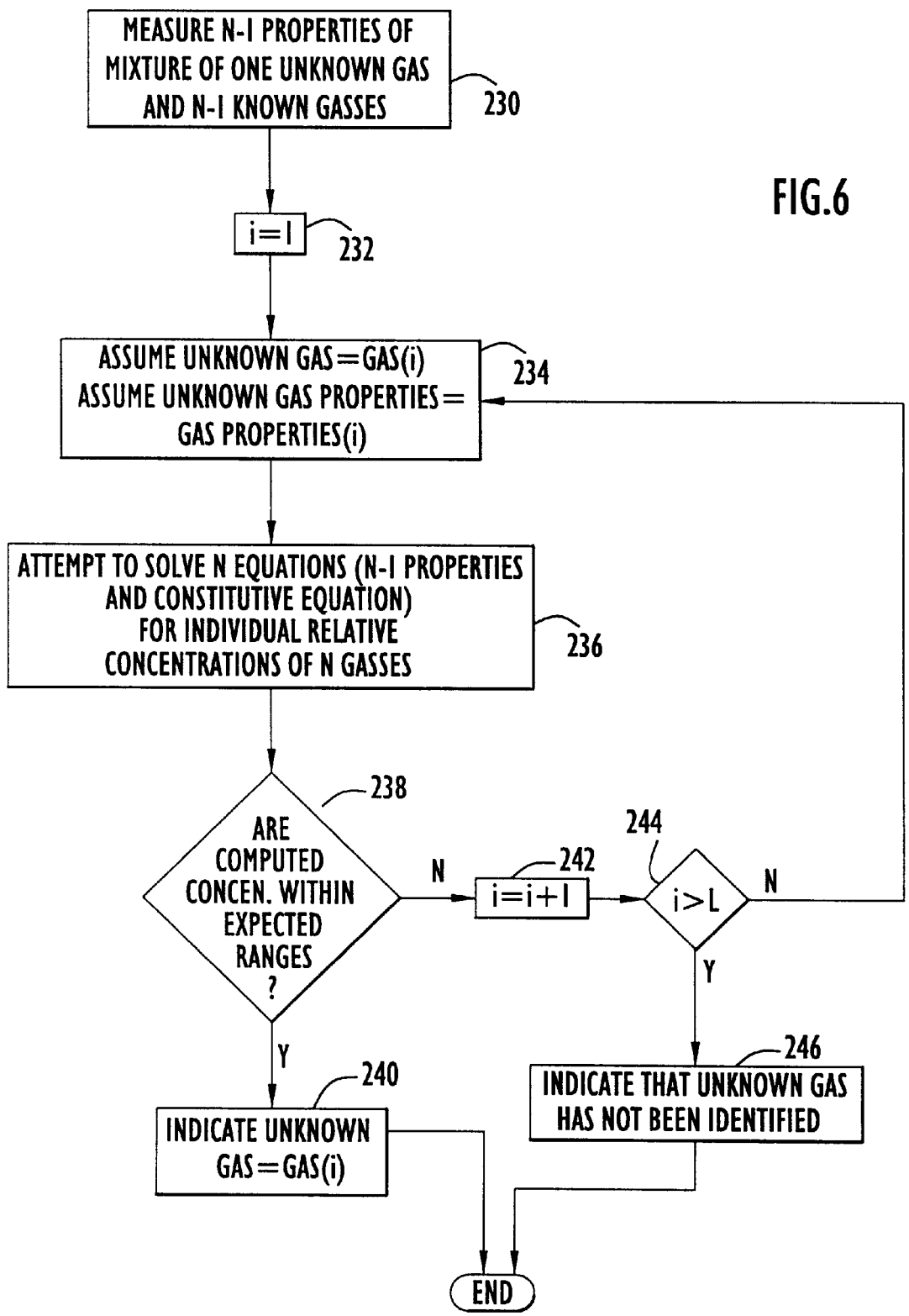
FIG. 6 is a functional flow diagram illustrating the processing steps required to determine the probable identity of an unknown gas in a mixture of gasses in accordance with another embodiment of the present invention.

More specifically, as shown in FIG. 6, according to this embodiment, in a first step 230, N−1 properties of the mixture are determined using an N-gas analyzer. For example, the density, viscosity, specific heat and dielectric constant of the mixture as a whole can be determined using the above-described oscillator-capillary-sonic oscillator sensors. Further, concentrations of individual gasses can be determined using other, conventional sensors or other properties of the mixture as whole, which properties relate to relative concentrations. Also, in the case of anesthesia administration, the above-described technique for discriminating carbon dioxide and nitrous oxide can be employed. For example, the mixture could consist of six (N=6) gasses: nitrogen, oxygen, carbon dioxide/nitrous oxide, water vapor and an anesthesia agent, where the anesthesia agent is assumed to be initially unknown. The four properties measured by the gas analyzer could be, for example: density, viscosity, specific heat and dielectric constant.

The unknown gas is then assumed to be one of a set of possible gasses. Specifically, a list of L gasses and their known properties are stored in a memory. For example, where the unknown gas is an anesthetic agent, a list of five or six anesthesia agents (e.g., halothane, enflurane, isoflurane, methoxyflurane, desflurane, sevoflurane) and their properties (e.g., density, viscosity, specific heat and dielectric constant) are stored in a look-up table in a memory. In step 232, a counter i, which indexes the look-up table, is initialized to a value of 1, corresponding to a first anesthetic agent $A_1$ in the look-up table (i.e., the default agent).

In step 234, the value of counter i (initially equal to one11 is used to retrieve the name and properties of gas i in the look-up table, and the identity of the unknown gas is assigned (i.e., temporarily assumed to be) that of gas i, with the properties of the unknown gas being assigned the values of the properties of gas i retrieved from the look-up table. Initially, the value of i is set to one; thus, the unknown gas is assumed to be the default gas $A_1$ in the look-up table, and the properties of the unknown gas are assumed to be those of the default gas $A_1$.

In step 236, using the assumption that the unknown gas has the properties of the gas $A_i$, the N−1 properties are used to form N−1 equations relating to the relative concentrations, which, together with the constitutive equation (equation #) form N equations, and an attempt is made to solve the N equations for the relative concentrations of the constituents of the mixture. For example, the equations for density, viscosity, specific heat, dielectric constant and the constitutive equation can be used to calculate the relative concentrations of nitrogen, oxygen, carbon dioxide/nitrous oxide, water vapor and gas $A_i$.

It has been found by the present inventor that, provided that a sufficient concentration (e.g., at least approximately 0.5–5%) of the unknown gas is present, the equations yield individual gas concentrations that fall within expected or reasonable ranges only when the properties of the unknown gas are assumed to be those of the correct gas in the equations. If the properties of the wrong gas are used, the equations yield at least one gas concentration that is not within its expected range or, mathematically, is not between zero and one. Thus, if the solution of the equations yields concentrations within expected ranges, it is assumed that the unknown gas is indeed the gas $A_i$. In practice, expected ranges of concentrations of individual gasses can be stored or pre-programmed into the system for comparison with the computed concentrations in order to determine whether the computed concentrations are reasonable. Other out of bounds conditions may be very high $CO_2$ or agent concentrations.

In step 238, if the solution to the equations yields concentrations that are within expected ranges, it is determined that the unknown gas is gas $A_i$. In this case, in step 240, it is indicated (on a display or the like) that the unknown gas is gas $A_i$, and the identification process ends.

If the solution to the equations fails to converge to meaningful concentration values (i.e., at least one constituent concentration is outside its expected range), it is determined that the unknown gas is not gas $A_i$. In this case, in step 242, the index counter i is incremented, and in step 244, the index counter i is compared to the number L of gasses in the look-up table. If the index counter i is not greater than L, processing returns to step 234, and the process is repeated with the incremented value of i. If, on the other hand, the index counter i is determined to be greater than L in step 244, it is indicated in step 246 (on a display and/or by aural alarm) that the unknown gas has not been identified, and the identification process ends.

The approach of the present invention provides a simple apparatus and method to measure concentrations of several medical gasses and to identify individual gasses at a relatively low cost. Although the above description is primarily concerned with medical gas analyzers, the present invention is not limited to the preferred embodiment but is applicable to other gas analysis applications, including, but not limited to, industrial production of gasses, atmospheric analysis, pollution tracking and other applications for the detection and analysis of chemical and biological agents. In addition, the present invention is not limited to a specific number of gasses that are in a mixture or for that matter only fluidic sensors, but rather, since bulk properties of gasses can be measured using a variety of low cost electronic and hybrid electro-fluidic devices, the present invention may extend to low cost scientific gas analysis of large numbers of gasses.

Furthermore, the present invention is not limited to the analysis of only gasses because it should be recognized that substantially the same methods and apparatus may be applied to the analysis of mixtures of liquid fluids as well, as long as sufficient differences in mixture bulk properties will occur due to the changes of concentrations of the constituents of the fluids. More specifically, the density and viscosity of a liquid can be measured and determined in accordance with well-known relationships with measurements from the fluidic sensors (e.g., flow meter, capillary, orifice, etc.). Other suitable sensors can be used to measure other properties of a mixture of liquids that relate to constituent concentrations or which can be used to uniquely identify an unknown liquid constituent in accordance with the above described techniques.

Having described preferred embodiments of new and improved methods and apparatus for real time fluid analysis, it is believed that other modifications., variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. An apparatus for determining individual concentrations of at least L fluid constituents and identities of at least M fluid constituents of a mixture of fluids, where L and M are non-negative integers, the apparatus comprising:

a plurality of sensors adapted to measure physical characteristics of the mixture, said sensors including a pressure drop flow element which measures a pressure drop of the mixture across an orifice, an acoustic flowmeter which measures the speed of sound in the mixture and the flow velocity of the mixture, and a surface acoustic wave (SAW) device; and a processor configured to: determine values of N−1 properties of the mixture from the measured physical characteristics, where N is equal to L+M; establish N−1 equations relating the individual concentrations of the fluid constituents to the N−1 properties of the mixture; and solve the N−1 equations and a constitutive equation for the individual concentrations of L of the fluid constituents and for identities of M of the fluid constituents.

2. The apparatus of claim 1, wherein:

said processor calculates the viscosity of the mixture from a measured resonance of said SAW device;

said processor calculates the density of the mixture from said pressure drop and the flow velocity; and said processor calculates the specific heat of the mixture from the density and the speed of sound, wherein said properties of the mixture include the density, viscosity and specific heat.

3. The apparatus of claim 2, wherein:

said sensors further include a capacitor whose capacitance varies in accordance with the dielectric constant of the mixture; and said processor calculates the dielectric constant of the mixture from the capacitance, the dielectric constant being one of said properties of the mixture.

4. The apparatus of claim 2, wherein:

said sensors further include a refractive index sensor whose output varies in accordance with the refractive index of the mixture; and said processor calculates the refractive index of the mixture from the output of the refractive index sensor, the refractive index being one of said properties of the mixture.

5. The apparatus of claim 2, wherein said plurality of sensors further includes:

a temperature sensor adapted to measure the ambient temperature of the mixture; and a pressure sensor adapted to measure ambient pressure of the mixture.

6. The apparatus of claim 1, wherein the mixture of fluids comprises N fluids, and wherein said processor solves the N−1 equations and the constitutive equation for the individual concentrations of the fluid constituents in real time.

7. The apparatus of claim 1, wherein the fluid constituents of the mixture of fluids are gasses respired during anesthesia administration.

8. The apparatus of claim 1, wherein, said mixture includes an N+1th fluid and said processor determines a combined concentration of two of said fluid constituents, said processor determining the individual concentrations of the two fluid constituents by determining changes in the combined concentration of the two fluid constituents over time.

9. The apparatus of claim 1, wherein:
the identity of one of the fluid constituents is initially unknown;
said processor establishes the N−1 equations by assuming that the unknown fluid constituent is one of P fluids whose properties are known, where P is a positive integer;
said processor determines that the unknown fluid constituent is said one of the P fluids if the individual concentrations solved for fall within respective predetermined concentration ranges; and
if the individual concentrations solved for do not fall within the respective predetermined concentration ranges, said processor establishes N−1 equations relating the individual concentrations of the fluid constituents to the N−1 properties of the mixture by assuming the unknown fluid constituent is different ones of said P fluids and solves the N−1 equations and a constitutive equation for the individual concentrations of the fluid constituents, until the individual concentrations solved for fall within the respective predetermined concentration ranges or until the unknown fluid constituent has been assumed to be every one of said P fluids.

10. The apparatus of claim 1, wherein:
the identity of one of the fluid constituents is initially unknown;
said processor determines a value of an Nth property of the mixture from the measured physical characteristics;
said processor establishes the N−1 equations by assuming that the unknown fluid constituent is one of P fluids whose properties are known, where P is a positive integer;
said processor calculates a value of an Nth property of the unknown fluid constituent from an equation relating the Nth property of the mixture to individual concentrations of the constituent components, where the Nth property of the mixture is not used to establish the N−1 equations;
said processor determines whether the calculated value of the Nth property of the unknown fluid constituent matches, to within a predetermined threshold, a known value of the Nth property of said one of the P fluids;
said processor determines that the unknown fluid constituent is said one of the P fluids if a match is found; and
if a match is not found, said processor establishes N−1 equations relating the individual concentrations of the fluid constituents to the N−1 properties of the mixture by assuming the unknown fluid constituent is different ones of said P fluids and solves the N−1 equations and a constitutive equation for the individual concentrations of the fluid constituents, until a match is found or until a match has been attempted with all of said P fluids.

11. The apparatus of claim 1, wherein:
said mixture comprises P+N fluids, where P is a positive integer;
individual concentrations of P of the fluid constituents are known prior to establishing the N−1 equations; and
said processor establishes the N−1 equations relating the individual concentrations of the fluid constituents, including the known individual concentrations of the P fluid constituents, to the N−1 properties of the mixture.

12. The apparatus of claim 1, wherein said processor determines the individual concentrations of L of the fluid constituents in real time.

13. The apparatus of claim 1, wherein the mixture of fluids comprises inhaled or exhaled gasses, and said processor determines at least one of uptake, consumption and production of inhaled or exhaled gasses.

14. The apparatus of claim 1, wherein said pressure drop flow element, said acoustic flowmeter and said surface acoustic wave (SAW) device are disposed within a main gas flow passage of a breathing circuit.

15. A method of determining individual concentrations of at least L fluid constituents and identities of at least M fluid constituents of a mixture of fluids flowing in a stream, where L and M are non-negative integers, the method comprising the steps of:
(a) measuring a pressure drop of the mixture with a pressure-drop device;
(b) determining mixture flow rate and the speed of sound in the mixture from acoustic flowmeter measurements;
(c) determining mixture viscosity from resonance of a surface acoustic wave (SAW) device;
(d) determining mixture density from the pressure drop, the mixture flow rate and the mixture viscosity;
(e) determining mixture specific heat from the mixture density and the speed of sound in the mixture;
(f) establishing at least three equations relating individual concentrations of the fluid constituents to at least three properties of the mixture, three of the at least three equations respectively relating the individual concentrations of the fluid constituents to the mixture viscosity, the mixture density and the mixture specific heat; and
(g) solving said at least the three equations and a constitutive equation for the individual concentrations of L of the fluid constituents and for identities of M of the fluid constituents.

16. The method of claim 15, wherein the mixture of fluids comprises inhaled or exhaled gasses, the method further comprising:
determining at least one of uptake, consumption and production of inhaled or exhaled gasses.

17. The method of claim 15, further comprising:
(h) determining the dielectric constant of the mixture from capacitance of a capacitor; wherein;
step (f) includes establishing a fourth equation relating the individual concentrations of the fluid constituents to the dielectric constant of the mixture; and
step (g) includes solving at least four equations and a constitutive equation for the individual concentrations of L of the fluid constituents and for identities of M of the fluid constituents.

18. The method of claim 17, further comprising:
(i) determining the refractive index of the mixture, wherein;
step (f) includes establishing a fifth equation relating the individual concentrations of the fluid constituents to the refractive index of the mixture; and
step (g) includes solving at least five equations and a constitutive equation for the individual concentrations of L of the fluid constituents and for identities of M of the fluid constituents.

19. The method of claim 15, further comprising:
(h) determining the refractive index of the mixture, wherein;
  step (f) includes establishing a fourth equation relating the individual concentrations of the fluid constituents to the refractive index of the mixture; and
  step (g) includes solving at least four equations and a constitutive equation for the individual concentrations of L of the fluid constituents and for identities of M of the fluid constituents.

20. The method of claim 15, further comprising:
measuring the ambient temperature of the mixture; and
measuring the ambient pressure of the mixture.

21. The method of claim 15, wherein the mixture of fluids comprises N fluids, and step (g) includes solving the N−1 equations and the constitutive equation for the individual concentrations of the fluid constituents in real time.

22. The method of claim 15, wherein the fluid constituents of the mixture of fluids are gasses respired during anesthesia administration.

23. The method of claim 15, wherein, said mixture includes an N+1th fluid and step (g) includes determining a combined concentration of two of said fluid constituents, the method further comprising:
  (h) determining the individual concentrations of the two fluid constituents by determining changes in the combined concentration of the two fluid constituents over time.

24. The method of claim 15, wherein the identity of one of the fluid constituents is initially unknown, and wherein step (f) includes assuming that the unknown fluid constituent is one of P fluids whose properties are known, where P is a positive integer, the method further comprising the steps of:
  (h) indicating that the unknown fluid constituent is said one of the P fluids if the individual concentrations solved for in step (g) fall within respective predetermined concentration ranges; and
  (i) if the individual concentrations solved for in step (g) do not fall within the respective predetermined concentration ranges, repeating steps (f) through (h) by assuming the unknown fluid constituent is different ones of said P fluids, until the individual concentrations solved for in step (g) fall within the respective predetermined concentration ranges or until the unknown fluid constituent has been assumed to be every one of said P fluids.

25. The method of claim 15, wherein:
the identity of one of the fluid constituents is initially unknown; and
step (f) includes assuming that the unknown fluid constituent is one of P fluids whose properties are known, where P is a positive integer;
the method further comprising the steps of:
  (h) determining a value of an additional property of the mixture from measured characteristics;
  (i) calculating a value of an additional property of the unknown fluid constituent from an equation relating the additional property of the mixture to individual concentrations of the constituent components, where the additional property of the mixture is not used in step (f);
  (j) determining whether the calculated value of the additional property of the unknown fluid constituent matches, to within a predetermined threshold, a known value of the additional property of said one of the P fluids;
  (k) if a match is found in step (j), indicating that the unknown fluid constituent is said one of the P fluids; and
  (l) if a match is not found in step (j), repeating steps (f), (g), (i), (j) and (k) with different ones of said P fluids until a match is found or until a match has been attempted with all of said P fluids.

26. The method of claim 15, wherein:
said mixture comprises P+N fluids, where P is a positive integer; and
individual concentrations of P of the fluid constituents are known prior to establishing N−1 equations, the method further comprising:
  establishing the N−1 equations relating the individual concentrations of the fluid constituents, including the known individual concentrations of the P fluid constituents, to the N−1 properties of the mixture.

27. The method of claim 15, where plural fluids whose ratios of concentrations do not substantially vary over time are treated as a single fluid constituent of the mixture.

28. An apparatus for determining individual concentrations of at least L fluid constituents and identities of at least M fluid constituents of a mixture of fluids, where L and M are non-negative integers, the apparatus comprising:
means for measuring physical characteristics of the mixture, including: means for measuring a pressure drop of the mixture; means for acoustically measuring mixture flow rate; means for measuring the speed of sound in the mixture; and means for measuring viscosity of the mixture; and
means for determining values of N−1 properties of the mixture from the measured physical characteristics, where N is equal to L+M; said means for determining establishing N−1 equations relating the individual concentrations of the fluid constituents to the N−1 properties of the mixture, and solving the N−1 equations and a constitutive equation for the individual concentrations of L of the fluid constituents and for identities of M of the fluid constituents.

29. The apparatus of claim 28, wherein:
said means for determining calculates the density of the mixture from the pressure drop and the flow rate; and
said means for determining calculates the specific heat of the mixture from the density and the speed of sound, wherein said properties of the mixture include the density, viscosity and specific heat.

30. The apparatus of claim 29, wherein:
said means for measuring physical characteristics of the mixture further includes means for determining the dielectric constant of the mixture, the dielectric constant being one of said properties of the mixture.

31. The apparatus of claim 29, wherein:
said means for measuring physical characteristics of the mixture further includes means for determining a refractive index of the mixture, the refractive index being one of said properties of the mixture.

32. The apparatus of claim 29, wherein said means for measuring physical characteristics of the mixture further includes:
means for measuring the ambient temperature of the mixture; and
means for measuring the ambient pressure of the mixture.

33. The apparatus of claim 28, wherein the mixture of fluids comprises N fluids, and wherein said means for determining solves the N−1 equations and the constitutive equation for the individual concentrations of the fluid constituents in real time.

34. The apparatus of claim 28, wherein the fluid constituents of the mixture of fluids are gasses respired during anesthesia administration.

35. The apparatus of claim 28, wherein, said mixture includes an N+1th fluid and said means for determining determines a combined concentration of two of said fluid constituents and determines the individual concentrations of the two fluid constituents by determining changes in the combined concentration of the two fluid constituents over time.

36. The apparatus of claim 28, wherein:

the identity of one of the fluid constituents is initially unknown;

said means for determining establishes the N−1 equations by assuming that the unknown fluid constituent is one of P fluids whose properties arc known, where P is a positive integer;

said means for determining determines that the unknown fluid constituent is said one of the P fluids if the individual concentrations solved for fall within respective predetermined concentration ranges; and if the individual concentrations solved for do not fall within the respective predetermined concentration ranges, said means for determining establishes N−1 equations relating the individual concentrations of the fluid constituents to the N−1 properties of the mixture by assuming the unknown fluid constituent is different ones of said P fluids and solves the N−1 equations and a constitutive equation for the individual concentrations of the fluid constituents, until the individual concentrations solved for fall within the respective predetermined concentration ranges or until the unknown fluid constituent has been assumed to be every one of said P fluids.

37. The apparatus of claim 28, wherein:

the identity of one of the fluid constituents is initially unknown;

said means for determining determines a value of an Nth property of the mixture from the measured physical characteristics;

said means for determining establishes the N−1 equations; by assuming that the unknown fluid constituent is one of P fluids whose properties are known, where P is a positive integer;

said means for determining calculates a value of an Nth property of the unknown fluid constituent from an equation relating the Nth property of the mixture to individual concentrations of the constituent components, where the Nth property of the mixture is not used to establish the N−1 equations;

said means for determining determines whether the calculated value of the Nth property of the unknown fluid constituent matches, to within a predetermined threshold, a known value of the Nth property of said one of the P fluids;

said means for determining determines that the unknown fluid constituent is said one of the P fluids if a match is found; and if a match is not found, said means for determining establishes N−1 equations relating the individual concentrations of the fluid constituents to the N−1 properties of the mixture by assuming the unknown fluid constituent is different ones of said P fluids and solves the N−1 equations and a constitutive equation for the individual concentrations of the fluid constituents, until a match is found or until a match has been attempted with all of said P fluids.

38. The apparatus of claim 28, wherein:

said mixture comprises P+N fluids, where P is a positive integer;

individual concentrations of P of the fluid constituents are known prior to establishing the N−1 equations; and said means for determining establishes the N−1 equations relating the individual concentrations of the fluid constituents, including the known individual concentrations of the P fluid constituents, to the N−1 properties of the mixture.

39. The apparatus of claim 28, wherein said means for determining determines the individual concentrations of L of the fluid constituents in real time.

40. The apparatus of claim 28, wherein the mixture of fluids comprises inhaled or exhaled gasses, and said means for determining determines at least one of uptake, consumption and production of inhaled or exhaled gasses.

41. The apparatus of claim 28, wherein said means for measuring physical characteristics of the mixture are disposed within a main gas flow passage of a breathing circuit.

* * * * *